United States Patent [19]

Hauser et al.

[11] Patent Number: 4,536,080
[45] Date of Patent: Aug. 20, 1985

[54] DEVELOPER MATERIAL END OF LIFE SENSING

[75] Inventors: Oscar G. Hauser, Rochester; Dusan G. Lysy, Fairport; Richard F. Koehler, Jr., Webster, all of N.Y.

[73] Assignee: Xerox Corporation, Stamford, Conn.

[21] Appl. No.: 524,612

[22] Filed: Aug. 19, 1983

[51] Int. Cl.³ .............................................. G03G 15/08
[52] U.S. Cl. ............................. 355/14 D; 355/3 DD; 118/689; 118/691
[58] Field of Search ........... 355/14 D, 3 DD; 430/30, 430/120, 125; 118/689, 691, 624, 644, 653, 657, 658, 665, 668, 669, 690

[56] References Cited

U.S. PATENT DOCUMENTS

| 4,431,300 | 2/1984 | Snelling | 355/14 D |
| 4,447,145 | 5/1984 | Snelling et al. | 355/14 D |
| 4,462,680 | 7/1984 | Ikeda | 355/14 D |
| 4,466,731 | 8/1984 | Champion et al. | 355/14 D |

FOREIGN PATENT DOCUMENTS

47128270 7/1974 Japan .
51-46163 10/1977 Japan .
53-22472 9/1979 Japan .

Primary Examiner—A. C. Prescott
Attorney, Agent, or Firm—H. Fleischer; J. E. Beck; R. Zibelli

[57] ABSTRACT

An electrophotographic printing machine in which a developer roller transports a developer material comprising carrier granules and toner particles closely adjacent to an electrostatic latent image recorded on a photoconductive surface so as to develop the latent image with the toner particles. A member is positioned closely adjacent to the developer roller to attract the toner particles to at least one surface thereof. A beam of energy is transmitted through the member onto the surface on which the toner particles adhere. The internal angle of incidence of the beam of energy is greater than the critical angle of incidence of the member. The intensity of the beam of energy internally reflected through the member is detected. A signal indicative of the quantity of toner particles attracted to the surface of the member is generated. The signal is processed and a signal transmitted indicating the end of the useful life of the developer material.

22 Claims, 5 Drawing Figures

DEVELOPER MATERIAL END OF LIFE SENSING

This invention relates generally to an electrophotographic printing machine, and more particularly concerns an apparatus for sensing the condition of the developer material to determine when the end of the useful life thereof is approaching.

Generally, the process of electrophotographic printing includes charging a photoconductive member to a subtantially uniform potential so as to sensitize the surface thereof. The charged portion of the photoconductive surface is exposed to a light image of an original document being reproduced. This records an electrostatic latent image on the photoconductive member corresponding to the informational areas contained in the original document. After the electrostatic latent image is recorded on the photoconductive member, the latent image is developed by bringing a developer material into contact therewith. This forms a powder image on the photoconductive member which is subsequently transferred to a copy sheet. Finally, the powder image is heated to permanently affix it to the copy sheet in image configuration.

Generally, the developer material employed in an electrophotographic printing machine comprises carrier granules having toner particles adhering triboelectrically thereto. This two-component mixture is brought into contact with the photoconductive surface. The toner particles are attracted from the carrier granules to the latent image. It is clear that the developer material is an essential ingredient in the electrophotographic printing machine. As the useful life of the developer material approaches an end, the quality of the copies being reproduced in the printing machine starts to degrade. Thus, it would be highly desirable to be able to detect when the useful life of the developer material was terminating. Machine service costs are severely impacted by the failure of the developer material not only from the perspective of a service call but also from the increased frequency of service calls for copy quality reasons. These copy quality related calls may be caused by dirt generation from the developer material which is nearing the end of its useful life. Therefore, the developer material is frequently changed without knowing the condition thereof to prevent the generation of dirt. Whereas this can be wasteful of developer material, if useful developer material is discarded, it might be presently economically justifiable to save additional service calls. However, a device which could indicate the status of the developer material and specify its proximity to the end of its useful life would be very helpful from two perspectives. First, if the signals from the device were monotonic with developer material degradation then the operator could be warned via a display that a developer material service call should be shortly made. Secondly, if the machine continued in operation after the warning had been displayed, then the machine could shut down at a predetermined point which would prevent total system contamination. In addition, it would be highly desirable if a device of this type would also control the concentration of toner particles within the developer material to maintain the desired developability characteristics. To truly regulate developability so as to optimize copy quality, development of the latent image must be simulated. Various techniques have been devised for measuring the concentration of toner particles within a developer mixture. The following disclosures appear to be relevant:

Japanese Patent Application No. 47-128270
  Applicant: Canon, Inc.
  Application Date: Nov. 7, 1972
  Laid-Open No. 49-84031
  Laid-Open Date: July 20, 1974
Japanese Patent Application No. 51-46163
  Applicant: Canon, Inc.
  Application Date: Apr. 23, 1976
  Laid-Open No. 52-129527
  Laid-Open Date: Oct. 31, 1977
Japanese Patent Application No. 53-22472
  Applicant: Ricoh Company
  Application Date: Feb. 28, 1978
  Laid-Open No. 54-115240
  Laid-Open Date: Sept. 7, 1979
U.S. Pat. No. 4,431,300
  Patentee: Snelling
  Issued Feb. 14, 1984
U.S. Pat. No. 4,447,145
  Patentee: Snelling et al.
  Issued: May 8, 1984

The relevant portions of the foregoing disclosures may be briefly summarized as follows:

Canon (Japanese Patent Application No. 47-128270) describes a flat plate positioned so that developer material on a magnetic brush contacts a flat area on the plate. Light rays are transmitted onto the flat area and reflected to a photodetector. In this way, the concentration of toner in the developer material is sensed.

Canon (Japanese Patent Application No. 51-46163) discloses a light permeable separation wall contacting developer material on a magnetic brush. The light permeable wall has an electrically conductive layer on its surface. Light rays are reflected from the wall to a photodetector. The light reflected to the photodetector is measured under two different states, i.e. when the electrical field attracts the toner particles and repels the toner particles.

Ricoh describes an equilateral triangle with the electrodes being made of a glass plate having an electrically conductive coating in two metal plates. The electrodes are insulated from one another with developer material passing within the triangle. A lamp is located at the apex of the metal plates with a pair of photodetectors being positioned on the other side of the glass plate. The plate is electrically biased with the polarity being alternately reversed. The detector signals are an indication of the performance capabilities of the developer material.

Both Snelling and Snelling et al. disclose a prism having a light source for transmitting light rays onto an electrically conductive layer having toner particles adhering thereto. The internally reflected light is measured by a photodector and the quantity of toner particles detected to provide an indication of the developability of toner particles within the developer material.

In accordance with one aspect of the present invention, there is provided an electrophotographic printing machine of the type having a developer roller transporting a developer material comprising at least carrier granules having toner particles adhering triboelectrically thereto closely adjacent to an electrostatic latent image recorded on a photoconductive surface so as to develop the latent image with the toner particles. A member, positioned closely adjacent to the developer roller, is adapted to attract at least a portion of the toner particles to at least one surface thereof. Means transmit a beam of energy through the member onto the surface having the toner particles adhering thereto with the internal angle of incidence of the beam of energy being greater than the critical angle of incidence of the member. Means detect the intensity of the beam of energy internally reflected through the member. The detecting means generates a signal indicative of the quantity of toner particles attracted to the surface of the member. Means process the signal received from the detecting means and transmit a signal indicating the end of the useful life of the developer material.

Other features of the present invention will become apparent as the following description proceeds and upon reference to the drawings, in which.

While the present invention will hereinafter be described in connection with various embodiments thereof, it will be understood that it is not intended to limit the invention to these embodiments. On the contrary, it is intended to cover all alternatives, modifications and equivalents as may be included within the spirit and scope of the invention as defined by the appended claims.

Figure 1:
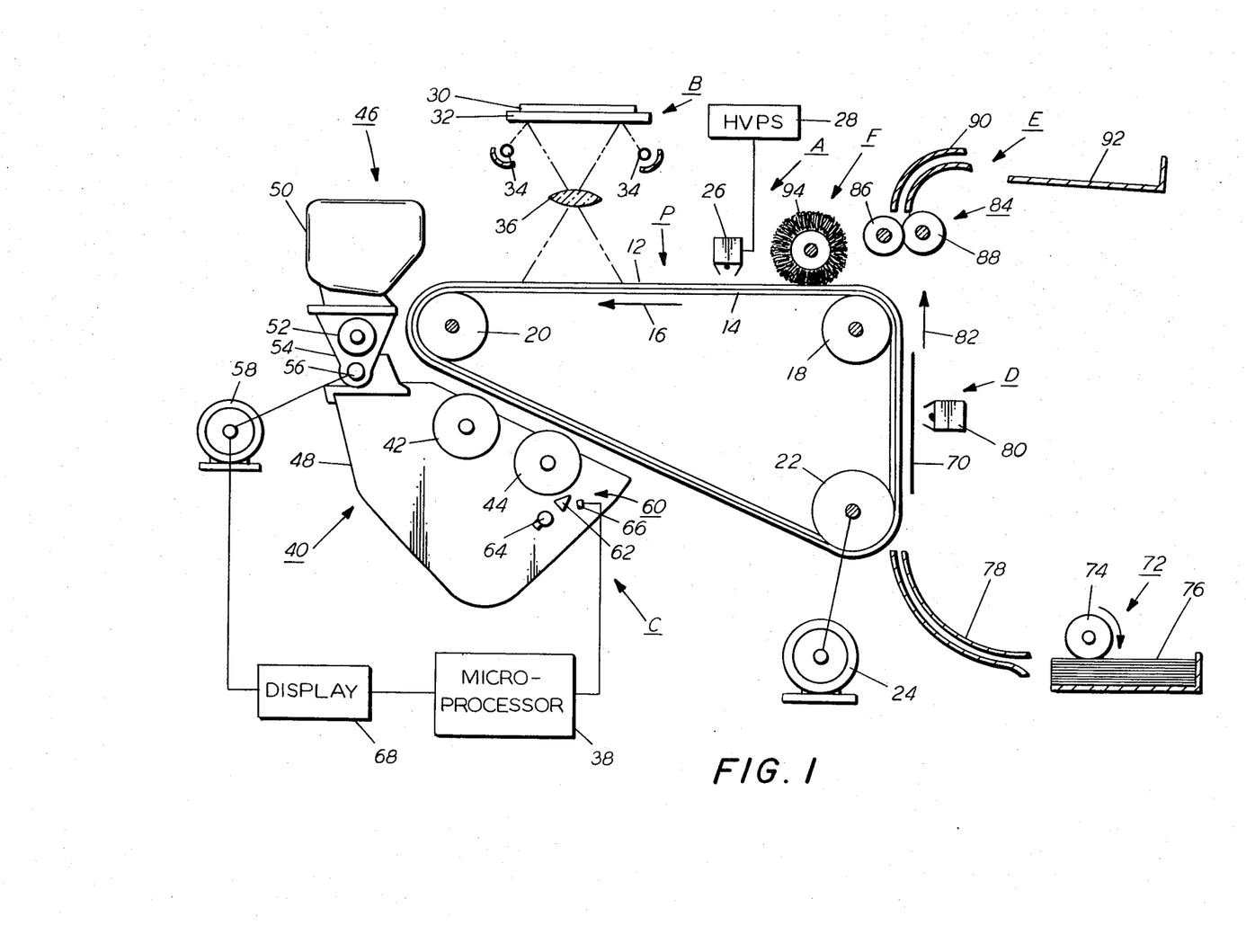
FIG. 1 is a schematic elevational view of an illustrative electrophotographic printing machine incorporating the apparatus of the present invention therein.

For a general understanding of the features of the present invention, reference is made to the drawings. In the drawings, like reference numerals have been used throughout to designate identical elements. FIG. 1 schematically depicts the various components of an illustrative electrophotographic printing machine incorporating the features of the present invention therein. It will become apparent from the following discussion that the apparatus of the present invention is equally well suited for use in a wide variety of machines and is not necessarily limited in its application to the particular embodiment shown herein.

Inasmuch as the art of electrophotographic printing is well known, the various processing stations employed in the FIG. 1 printing machine will be shown hereinafter schematically and their operation described briefly with reference thereto.

Referring now to FIG. 1, the illustrative electrophotographic printing machine employs a belt 10 having a photoconductive surface 12 deposited on a conductive substrate 14. Preferably, photoconductive surface 12 is made from a selenium alloy. Conductive substrate 14 is made preferably from an aluminum alloy which is electrically grounded. Belt 10 moves in the direction of arrow 16 to advance successive portions of photoconductive surface 12 sequentially through the various processing stations disposed about the path of movement thereof. Belt 10 is entrained about stripping roller 18, tension roller 20 and drive roller 22. Drive roller 22 is mounted rotatably and in engagement with belt 10. Motor 24 rotates roller 22 to advance belt 10 in the direction of arrow 16. Roller 22 is coupled to motor 24 by a suitable means such as a belt drive. Roller 22 includes a pair of opposed, spaced edge guides. The edge guides define a space therebetween which determines the desired path of movement of belt 10. Belt 10 is maintained in tension by a pair of springs (not shown) resiliently urging tension roller 20 against belt 10 with the desired spring force. Both stripping roller 18 and tension roller 20 are mounted to rotate freely.

Initially, a portion of belt 10 passes through charging station A. At charging station A, a corona generating device, indicated generally by the reference numeral 26, charges photoconductive surface 12 to a relatively high, substantially uniform potential. High voltage power supply 28 is coupled to corona generating device 26. Excitation of power supply 28 causes corona generating device 26 to apply a charge on photoconductive surface 12 of belt 10.

After photoconductive surface 12 of belt 10 is charged, the charged portion thereof is advanced through exposure station B. At exposure station B, an original document 30 is positioned facedown upon a transparent platen 32. Lamps 34 flash light rays onto original document 30. The light rays reflected from original document 30 are transmitted through lens 36 forming a light image thereof. Lens 36 focuses the light image onto the charged portion of photoconductive surface 12 to selectively dissipate the charge thereon. This records an electrostatic latent image on photoconductive surface 12 which corresponds to the informational areas contained within original document 30.

One skilled in the art will appreciate that a modulated beam of coherent light, i.e. a laser beam, may be used in lieu of the optical system to irradiate selected portions of the charged photoconductive surface. This records a latent image on the photoconductive surface corresponding to the electrical signal modulating the laser beam.

After the electrostatic latent image has been recorded on photoconductive surface 12, belt 10 advances the latent image to development station C. At development station C, a magnetic brush development system, indicated generally by the reference numeral 40, advances developer material into contact with the latent image. Preferably, magnetic brush development system 40 includes two magnetic brush developer rollers 42 and 44. Each roller advances developer material into contact with the latent image. These developer rollers form a brush of carrier granules and toner particles extending outwardly therefrom. The latent image attracts toner particles from the carrier granules forming a toner powder image on the latent image. As successive electrostatic latent images are developed, toner particles are depleted from the developer material. In addition, the developer material continues to age. Thus, the condition of the developer material is of paramount importance in order to maintain optimum copy quality. In order to furnish additional toner particles to the developer material, a toner particle dispenser, indicated generally by the reference numeral 46, dispenses toner particles. Toner dispenser 46 includes a container 50 storing a supply of toner particles therein. Foam roller 52, disposed in sump 54 beneath container 50 meters toner particles into auger 56. Motor 58 is coupled to auger 56. As motor 58 rotates, auger 56 advances toner particles for discharge into developer housing 48. Energization of motor 58 is regulated by microprocessor 38.

A sensor, indicated generally by the reference numeral 60, is positioned closely adjacent to developer roller 44. Sensor 60 comprises a substantially transparent prism 62 adapted to attract toner particles from the developer material adhering to developer roller 44. A light source 64 transmits light rays through prism 62 onto the toner particles adhering thereto. Light rays internally reflected through prism 62 are detected by light detector 66. Light detector 66 develops an electrical output signal which is transmitted to microprocessor 38. Microprocessor 38 develops an error signal which actuates motor 58 to dispense toner particles into developer housing 48. In addition, microprocessor 38 transmits a signal to display 68 indicating that the developer material is approaching the end of its useful life. One skilled in the art will appreciate that sensor 60 may be disposed adjacent developer roller 42 in lieu of roller 44. The detailed structure of sensor 60 will be described hereinafter with reference to FIGS. 2 through 5, inclusive.

After the electrostatic latent image is developed, belt 10 advances the toner powder image to transfer station D. A sheet of support material 70 is advanced to transfer station D by sheet feeding apparatus 72. Preferably, sheet feeding apparatus 72 includes a feed roll 74 contacting the uppermost sheet of a stack 76. Feed roll 74 rotates to advance the uppermost sheet from stack 76 into chute 78. Chute 78 directs the advancing sheet of support material into contact with photoconductive surface 12 of belt 10 in a timed sequence so that the toner powder image developed thereon contacts the advancing sheet of support material at transfer station D.

Transfer station D includes a corona generating device 80 which sprays ions onto the back side of sheet 70. This attracts the toner powder image from photoconductive surface 12 to sheet 70. After transfer, sheet 70 continues to move in the direction of arrow 82 onto a conveyor (not shown) which advances sheet 70 to fusing station E.

Fusing station E includes a fuser assembly, indicated generally by the reference numeral 84, which permanently affixes the transferred powder image to sheet 70. Preferably, fuser assembly 84 comprises a heated fuser roller 86 and a back-up roller 88. Sheet 70 passes between fuser roller 86 and back-up roller 88 with the toner powder image contacting fuser roller 86. In this manner, the toner powder image is permanently affixed to sheet 70. After fusing, chute 90 advances sheet 70 to catch tray 92 for subsequent removal from the printing machine by the operator.

After the sheet of support material is separated from the photoconductive surface of belt 10, the residual particles adhering to photoconductive surface 12 are removed therefrom at cleaning station F. Cleaning station F includes a rotatably mounted fibrous brush 94 in contact with photoconductive surface 12. The particles are cleaned from photoconductive surface 12 by the rotation of brush 94 in contact therewith. Subsequent to cleaning, a discharge lamp (not shown) floods photoconductive surface 12 with light to dissipate any residual electrostatic charge remaining thereon prior to the charging thereof for the next successive imaging cycle.

It is believed that the foregoing description is sufficient for purposes of the present application to illustrate the general operation of an electrophotographic printing machine incorporating the features of the present invention therein.

Figure 2:
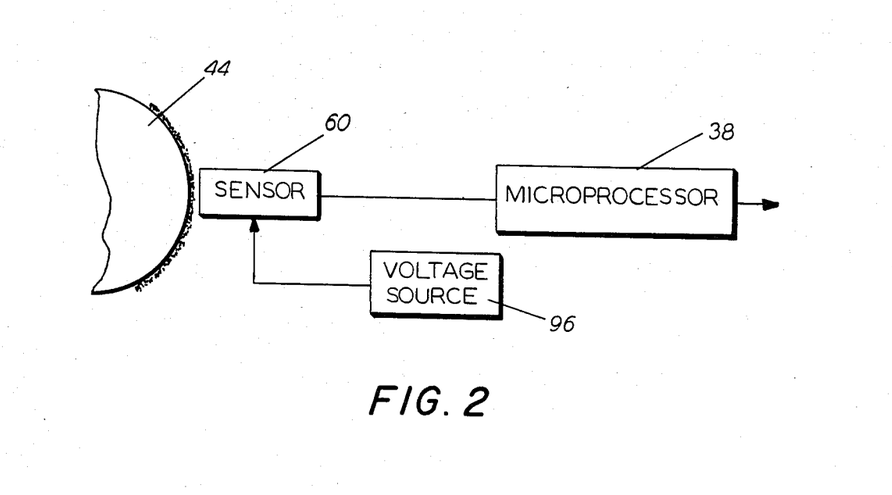
FIG. 2 is a block diagram used to determine the condition of the developer material employed in the FIG. 1 printing machine.

As illustrated in FIG. 2, sensor 60 is disposed closely adjacent to developer roller 44. As developer roller 44 transports developer material into contact with the latent image recorded on photoconductive surface 12, sensor 60 is also developed with toner particles. The quantity of toner particles is detected and an electrical output signal generated indicative thereof. Microprocessor 38 receives the electrical output signal from sensor 60 and processes it. Microprocessor 38 contains logic circuitry for generating the appropriate control signal dependent upon the type of developer material being employed, e.g. conductive or insulative. The output from microprocessor 38 actuates display 68 if the useful life of the developer material is terminated. In addition, the output from microprocessor 38 actuates motor 58 to dispense additional toner particles into the developer material as required. Voltage source 96 is coupled to sensor 60 so as to furnish the appropriate electrical biases to the conductive surface adhering to the prism, and to the light source and light detector.

Figure 3:
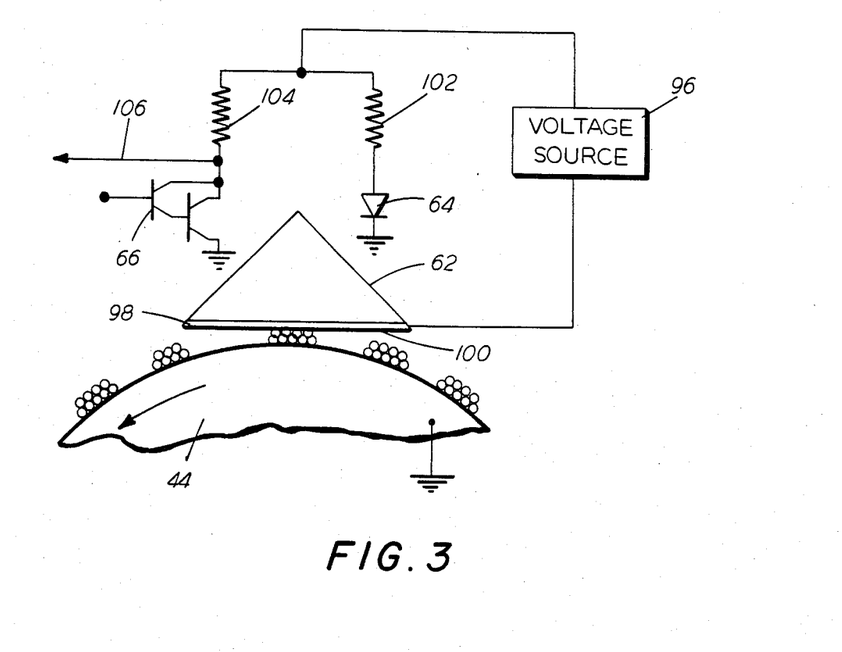
FIG. 3 is a schematic elevational view of the sensing circuitry associated with the FIG. 2 control system.

Referring now to FIG. 3, prism 62 is preferably a right triangular prism with the hypotenuse, i.e. surface 98, having a substantially transparent electrically conductive layer 100 adhering thereto. Preferably, electrically conductive layer 100 is a transparent tin oxide coating which is made by Pittsburgh Plate Glass under the trademark NESA or is made by the Corning Glass Company under the trademark Electroconductive. The angles of transparent prism 62 opposed from light source 64 and light detector 66 are equal and 45°. Voltage source 96 is coupled to electrically conductive layer 100 so as to electrically bias the surface of prism 62, thereby attracting toner particles being transported on developer roller 44 thereto. Light source 64 is preferably a light emitting diode with light detector 66 being a phototransistor. Light emitting diode 64 is coupled to another output from voltage source 96 by resistor 102. Similarly, phototransistor 66 is coupled to that output from voltage source 96 by resistor 104. Preferably, resistor 102 is about 560 ohms with resistor 104 being about 2200 ohms. The voltage applied across resistor 104 and phototransistor 66, which is connected in parallel with light emitting diode 64 and resistor 102, is preferably about 6 volts DC. Line 106 transmits the electrical output signal from phototransistor 66 to microprocessor 38.

In operation, phototransistor 62 senses the changes in internal reflection from the surface on which toner particles are developed. By Snell's law, internal reflectance occurs up to a critical angle. The critical angle is measured with respect to the normal to the surface. The critical angle, without particles is about 41.5° when the index of refraction of the prism is about 1.51. The internal angle of incidence of the light source must be greater than the critical angle in order to have the light rays internally reflected by the prism. Inasmuch as the presence of toner paticles on the surface replaces air, the index of refraction of the space immediately adjacent to conductive layer 100 is greater than one. Thus, the critical angle is greater than the critical angle in the absence of toner particles on the surface. As toner particle deposition occurs on conductive layer 100, the critical angle increases and the magnitude of the internally reflected light is reduced. Thus, light rays are prevented from being internally reflected by the toner particles adhering to electrically conductive layer 100 on surface 98 and the loss in internal reflectance is detected by phototransistor 66. It should be noted that not only may visible light rays be employed but longer wave radiation, such as infrared light sources, may also be utilized in this system. The presence of toner particles on conductive layer 100 causes a decrease in the detected light intensity which corresponds to a decrease in the effective internal reflectivity of the surface. The total "internal" reflected radiation field extends beyond the prism face into the air/toner space a distance on the order of the wavelength of light. This is the exponentially decaying evanescent field. Thus, there are two categories of energy coupling from the prism, one due to the intimate contact of the toner particles with the prism surface and another due to the toner particles located near the prism surface mediated by the evanescent field. In the first case, the internal reflectivity of the prism surface is reduced by transmission into the toner particles, characterized by an index of refraction and an absorption coefficient. The second operates by evanescent field coupling of energy from the prism surface to the toner particles rather than relying on intimate contact between the surface and the toner particles. It appears that the evanescent field effect dominates to produce the large signal sensitivity that has been found in this sensing apparatus.

Figure 4:
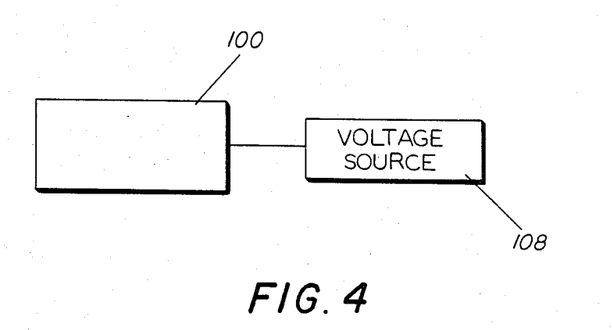
FIG. 4 is a schematic elevational view showing one embodiment of the pattern of conductive material adhering to a surface of the FIG. 3 prism.

Turning now to FIG. 4, there is shown one embodiment of the transparent electrically conductive layer 100 adhering to surface 98 of prism 62. As depicted thereat, electrically conductive layer 100 covers the entire surface of surface 98 and is substantially uniform. An electrically conductive layer of this type is employed when the developer material is insulative. When it is desired to vary the electrical bias applied to conductive layer 100, a dedicated voltage source 108 may be utilized. In determining the end of the useful life of an insulating developer material, both solid area and background development are monitored. Voltage source 108 electrically biases the conductive layer to a potential having substantially the same magnitude and polarity as that of the latent image recorded on photoconductive surface 12. The signal from phototransistor 66 is stored by microprocessor 38 for later comparison with a constant indicative of the permissible limits on solid area development. Voltage source 108 then electrically biases conductive layer 100 to a potential having substantially the same magnitude and polarity as the potential of the background regions recorded on photoconductive surface 12. The signal from phototransistor 66 is stored in microprocessor 38 for later comparison with a constant indicative of the limits on background development. Voltage source 108 then electrically biases conductive layer 100 to a potential having substantially the same magnitude and to an opposite polarity as that of the electrostatic latent image recorded on photoconductive surface 12. The signal from phototransistor 66 is stored by microprocessor 38 for subsequent comparison with a constant defining the limit of allowable development of toner particles with the wrong sign or unwanted polarity charge. Finally, voltage source 108 electrically biases conductive layer 100 to a potential having substantially the same magnitude and polarity as that of the electrical bias on developer roller 44. The signal from phototransistor 66 is stored in microprocessor 38 for comparison with the constant defining the limits on allowable background development. This latter signal is proportional to mechanical background. Immediately after the foregoing sequence of voltage steps, microprocessor 38 compares each of the stored signals from phototransistor 66 with the corresponding constant. If the signals from phototransistor 66 are less than the respective constants, or if the signal from phototransistor 66 corresponding to the allowable background limit is equal to the corresponding constant when voltage source 108 electrically biases conductive layer 100 to the potential of the background regions on photoconductive surface 12 and the other signals from phototransistor 66 are less than their respective constants, then motor 58 is energized causing toner dispenser 46 to discharge toner particles into development system 40 increasing the toner concentration of the developer material stored therein. After motor 58 has been energized for the appropriate period of time, the foregoing sequence of voltage steps is repeated until the signal from phototransistor 66, when conductive layer 100 is electrically baised by voltage source 108 to a potential of substantially the same magnitude and polarity as that of the latent image recorded on photoconductive surface 12, is equal to or greater than its respective constant. If, before the foregoing signal reaches this state, the signal from phototransistor 66, being compared with the allowable background constant when voltage source 108 electrically biases conductive layer 100 to the potential of the background region of photoconductive surface 12, is greater than this constant with the remaining signals from phototransistor 66 being less than their respective constants, microprocessor 38 transmits a signal energizing display 68 indicating that the useful life of the developer material has ended since the copies will have higher than allowable background and lower than allowable image.

Alternatively, if the signal from phototransistor 66 being compared with the constant defining the limits of the solid area development is equal to or less than the constant and the signal being compared with the allowable background constant, when voltage source 108 electrically biases conductive layer 100 to the potential of the background region of photoconductive surface 12, is less than this constant, with either of the remaining signals being greater than their respective constants, microprocessor 38 transmits a signal energizing display 68 to indicate that the useful life of the developer material has terminated. Under this latter condition, the amount of low charge toner or wrong sign toner in the developer material will cause toner clouding and machine contamination.

Finally, if the signal from phototransistor 66 is less than or equal to the constant defining the limits of solid area development with the other signals from phototransistor 66 being equal to or greater than their respective constants, microprocessor 38 transmits a signal energizing display 68 indicating the end of the useful life of the developer material.

Figure 5:
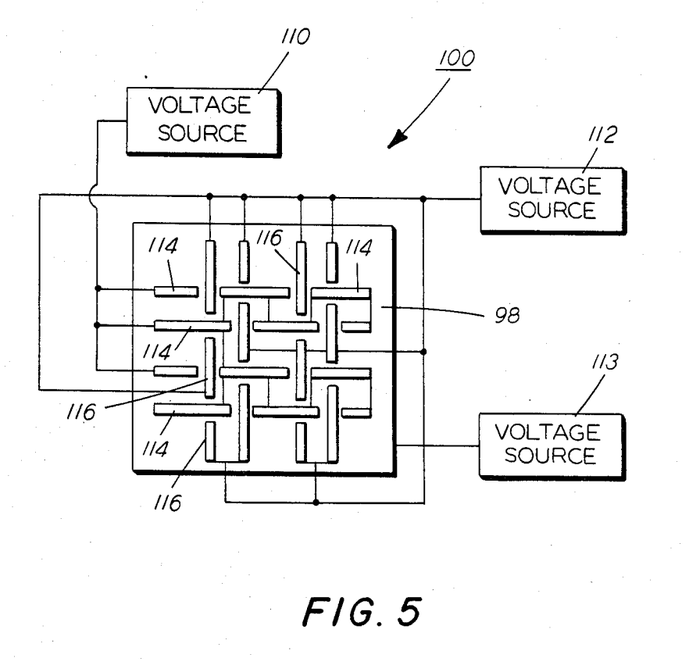
FIG. 5 is a schematic plan view showing another embodiment of the pattern of conductive material adhering to the surface of the FIG. 3 prism.

Turning now to FIG. 5, there is shown another embodiment of conductive layer 100. Generally, the embodiment depicted in FIG. 5 is employed when the developer material is conductive. As shown, conductive layer 100 comprises two sets of strip electrodes 114 and 116 on surface 98. Set 114 comprises a plurality of substantially parallel spaced apart electrodes. Set 114 is arranged to be parallel to the direction of movement of the developer material on developer roller 44. Set 116 comprises a plurality of parallel spaced electrode strips on surface 98. Strips 114, 116 and surface 98 are electrically insulated from one another. Set 116 is substantially perpendicular to set 114. Hence, set 116 is substantially perpendicular to the movement of developer material on developer roller 44.

Voltage sources 110, 112 and 113 electrically bias electrodes 114, 116 and surface 98, respectively. Electrodes 114 or 116 are alternatively electrically biased to one of four voltage levels. Electrode 114 is electrically biased to a potential substantially equal to the potential of the latent image recorded on photoconductive surface 12. Simultaneously, electrodes 116 and surface 98 are electrically biased to the potential of the non-image or background regions of photoconductive surface 12. The signal from the phototransistor 66 indicative of the internally reflected light rays from electrodes 114 is stored in microprocessor 38 for later comparison with a stored constant defining the limits of line development parallel to the process direction.

Electrodes 114 and 116, and surface 98 are then electrically biased to a voltage level substantially equal to the background potential on photoconductive surface 12. The signal from phototransistor 66 is stored in microprocessor 38 for subsequent comparison with a constant which determines the limits on background development.

Thereafter, electrodes 114 and 116, and surface 98 are electrically biased to a voltage level substantially equal to the potential of the latent image recorded on photoconductive surface 12. The signal from phototransistor 66 is stored in microprocessor 38 for subsequent comparison with a constant defining the limits of solid area development.

Electrodes 114 and 116, and surface 98 are, thereafter, electrically biased to a voltage level substantially equal to the potential electrically biasing developer roller 44. This creates a null electrical field to clean the toner particles from electrodes 114 and 116, and surface 98. The signal from phototransistor 66 is stored in microprocessor 38 for later comparison with a constant determining the limit on the amount of mechanical background development.

A voltage pulse, reversed in polarity and of substantially the same magnitude as the potential electrically biasing developer roller 44, is applied to electrodes 114 and 116, and surface 98. The signal from phototransistor 66 is stored in microprocessor 38 for subsequent comparison with a constant defining the allowable limits on the development of wrong sign toner.

The foregoing signals from phototransistor 66 relate to parallel lines and the solid area development characteristics of the conductive developer material. The foregoing sequence of voltages is repeated with the exception that initially electrodes 116 are electrically biased to a voltage level substantially equal to the potential of the latent image recorded on photoconductive surface 12. Simultaneously, electrodes 114 and surface 98 are electrically biased to the potential of the background regions of photoconductive surface 12. The signal from phototransistor 66, indicative of the internally reflected light rays from electrodes 116, is stored in microprocessor 38 for later comparison with a stored constant defining the limits of line development perpendicular to the process direction. The remainder of the voltage sequence is the same as that previously described.

Microprocessor 38 compares the signals from phototransistor 66 with the respective constants stored therein. If all of the signals from phototransistor 66 are less than their respective constants, motor 58 is energized causing toner dispenser 46 to discharge toner particles into the developer material to adjust the concentration of toner particles therein. Motor 58 is de-energized when any of the signals from phototransistor 66 are greater than their respective constant. However, if any of the signals from phototransistor 66, excluding the signal being compared to the constant defining the allowable limit of solid area development, are equal to or greater than their respective constants, microprocessor 38 transmits a signal energizing display 68 indicating that the useful life of the developer material has ended.

One skilled in the art will appreciate that the voltages electrically biasing electrodes 114 and 116, and surface 98 should not exceed the breakdown voltage of the conductive developer material.

Thus, it is clear that the apparatus of the present invention determines the approaching termination of the useful life of the developer material and whether additional toner particles are required therein. In this way, optimum developer material characteristics are continuously maintained within the printing machine insuring high quality copies.

It is, therefore, apparent that there has been provided in accordance with the present invention, an apparatus for determining the condition of the developer material used in an electrophotographic printing machine. This apparatus fully satisfies the aims and advantages hereinbefore set forth. While this invention has been described in conjunction with specific embodiments thereof, it is evident that many alternatives, modifications and variations will be apparent to those skilled in the art. Accordingly, it is intended to embrace all such alternatives, modifications and variations as fall within the spirit and broad scope of the appended claims.

What is claimed is:

1. An electrophotographic printing machine of the type having a developer roller transporting a developer material comprising at least carrier granules having toner particles adhering triboelectrically thereto closely adjacent to an electrostatic latent image recorded on a photoconductive surface so as to develop the latent image with toner particles, wherein the improvement includes:

a member, positioned closely adjacent to the developer roller, adapted to attract at least a portion of the toner particles to at least one surface thereof;

means for transmitting a beam of energy through said member onto the toner particles adhering to the surface thereof with the internal angle of incidence of the beam of energy being greater than the critical angle of incidence of said member;

means for detecting the intensity of the beam of energy internally reflected through said member, said detecting means generating a signal indicative of the quantity of toner particles attracted to the surface of said member; and means for processing the signal received from said detecting means and transmitting a signal indicating the end of the useful life of the developer material.

2. A printing machine according to claim 1, wherein said member includes:

a substantially transparent prism; and a substantially transparent, electrically conductive layer adhering to one surface of said prism.

3. A printing machine according to claim 2, wherein said member includes means for electrically biasing said conductive layer to attract the toner particles thereto.

4. A printing machine according to claim 3, wherein said transmitting means includes a light source transmitting light rays through said prism and said conductive layer onto the toner particles adhering thereto.

5. A printing machine according to claim 4, wherein said detecting means includes a light sensor positioned to receive light rays internally reflected through said prism.

6. A printing machine according to claim 5, wherein the developer material is substantially electrically insulative.

7. A printing machine according to claim 6, wherein said conductive layer is a substantially uniform area adhering to the surface of said prism.

8. A printing machine according to claim 7, wherein:
said biasing means electrically biases said conductive layer to a potential substantially of the same magnitude and polarity as the potential of the regions of the photoconductive surface not having the latent image recorded thereon; and
said processing means compares the signal received from said light sensor to a constant indicative of the maximum allowable background level on the photoconductive surface and transmits a signal indicating that the useful life of the developer material has ended if the signal from the light sensor is equal to or greater than the constant.

9. A printing machine according to claim 7, wherein:
said biasing means electrically biases said conductive layer to a potential having substantially the same magnitude and of an opposite polarity to that of the latent image having the toner particles attracted thereto; and
said processing means compares the signal from said light sensor to a constant indicative of the maximum allowable wrong sign toner particles and transmits a signal indicating that the useful life of the developer material has ended if the signal from the light sensor is equal to or greater than the constant.

10. A printing machine according to claim 7, wherein the developer roller is electrically biased.

11. A printing machine according to claim 10, wherein:
said biasing means electrically biases said conductive layer to a potential having substantially the same magnitude and polarity as that of the electrical bias on the developer roller; and
said processing means compares the signal from said light sensor to a constant indicative of the maximum allowable toner particles attracted to the photoconductive surface in the regions thereof not having the latent image recorded thereon and transmits a signal indicating that the useful life of the developer material has ended if the signal from the light sensor is greater than the constant.

12. A printing machine according to claim 5, wherein the developer material is substantially electrically conductive.

13. A printing machine according to claim 12, wherein said conductive layer includes:
a conductive surface;
a first set of substantially parallel electrodes disposed on said conductive surface and electrically insulated therefrom; and
a second set of substantially parallel electrodes, disposed on said conductive surface, said second set being substantially perpendicular to said first set and being electrically insulated from said conductive surface and said first set.

14. A printing machine according to claim 13, wherein:
said biasing means electrically biases said first set of electrodes and said second set of electrodes to a potential substantially equal to the potential of the latent image having the toner particles attracted thereto; and
said processing means compares the signal from said light sensor to constants indicative of the maximum allowable line growth and transmits a signal indicating that the useful life of the developer material has ended if the signal from the light sensor is equal to or greater than the respective constants.

15. A printing machine according to claim 13, wherein:
said biasing means electrically biases said first set of electrodes and said second set of electrodes to a potential having substantially the same magnitude and polarity as that of the regions of the photoconductive surface not having the latent image recorded thereon, and, thereafter, electrically biases said first set of electrodes and said second set of electrodes to a potential having substantially the same magnitude and polarity as that of the electrical bias on the developer roller; and
said processing means compares the signal from said light sensor when said first set of electrodes and said second set of electrodes are electrically biased to the potential of the regions of the photoconductive surface not having the latent image recorded thereon and to the potential having substantially the same magnitude and polarity as that of the electrical bias on the developer roller to a constant indicative of the maximum allowable toner particles attracted to the photoconductive surface and transmits a signal indicating that the useful life of the developer material has ended if the signal from the light sensor is equal to or greater than the constant.

16. A printing machine according to claim 13, wherein:
said biasing means electrically biases said first set of electrodes and said second set of electrodes to a potential having substantially the same magnitude and polarity as that of the electrical bias on the developer roller; and
said processing means compares the signal from said light sensor to a constant indicative of the maximum allowable background level and transmits a signal indicating that the useful life of the developer material has ended if the signal from the light sensor is equal to or greater than the constant.

17. A printing machine according to claim 13, wherein:
said electrical biasing means electrically biases said first set of electrodes and said second set of electrodes to a potential of substantially the same magnitude and opposite polarity to the potential of the latent image having toner particles attracted thereto; and
said processing means compares the signal received from said light sensor to a constant indicative of the maximum wrong sign toner particles on the photoconductive surface and transmits a signal indicating that the useful life of the developer material has ended if the signal from the light sensor is equal to or greater than the magnitude of the constant.

18. A printing machine according to claim 13, further including:

a housing storing a supply of developer material therein; and means, in communication with said processing means, for dispensing toner particles into said housing.

19. A printing machine according to claim 18, wherein:

said biasing means electrically biases said first set of electrodes to a potential having substantially the same magnitude and polarity as that of the latent image having toner particles attracted thereto; and said processing means compares the signal received from said light sensor to a constant indicative of the minimum required line development and transmits a signal to said dispensing means to dispense toner particles into said housing if the signal from the light sensor is less than the first constant.

20. A printing machine according to claim 19, wherein:

said biasing means electrically biases said conductive layer to a potential having substantially the same magnitude and polarity as that of the latent image having the toner particles attracted thereto; and said processing means compares the signal received from said light sensor to a constant indicative of the required minimum developed solid area on the photoconductive surface and transmits a signal indicating that the useful life of the developer material has eneded if the signal from the light sensor is less than the constant.

21. A printing machine according to claim 19, wherein:

said biasing means electrically biases said second set of electrodes to a potential having substantially the same magnitude and polarity as that of the latent image having toner particles attracted thereto; and said processing means compares the signal from said light sensor to a constant indicative of the required minimum line development and transmits a signal to said dispensing means to dispense toner particles into said housing if the signal from the light sensor is less than the constant.

22. A printing machine according to claim 19, wherein:

said biasing means electrically biases said conductive surface, said first set of electrodes and said second set of electrodes to a potential having substantially the same magnitude and polarity as that of the region of the photoconductive surface having the latent image recorded thereon; and said processing means compares the signal received from said light sensor to a constant indicative of the minimum required solid area development and transmits a signal to said dispensing means to dispense toner particles to said housing if the signal from the light sensor is less than the constant.

* * * * *